(12) United States Patent
Rosenkranz

(10) Patent No.: US 11,951,041 B2
(45) Date of Patent: Apr. 9, 2024

(54) POSITIONING DEVICE, LIGHT PROCESSOR HAVING SUCH A POSITIONING DEVICE, AND METHOD FOR LASER EYE SURGERY USING SUCH A LIGHT PROCESSOR

(71) Applicant: Physik Instrumente (PI) GmbH & Co. KG, Karlsruhe (DE)

(72) Inventor: Mathias Rosenkranz, Gernsbach (DE)

(73) Assignee: PHYSIK INSTRUMENTE (PI) GMBH & CO. KG, Karlsruhe (DE)

( * ) Notice: Subject to any disclaimer, the term of this patent is extended or adjusted under 35 U.S.C. 154(b) by 260 days.

(21) Appl. No.: 17/287,060

(22) PCT Filed: Sep. 26, 2019

(86) PCT No.: PCT/EP2019/076046
§ 371 (c)(1),
(2) Date: Apr. 20, 2021

(87) PCT Pub. No.: WO2020/083602
PCT Pub. Date: Apr. 30, 2020

(65) Prior Publication Data
US 2021/0378866 A1 Dec. 9, 2021

(30) Foreign Application Priority Data
Oct. 23, 2018 (DE) ...................... 10 2018 218 147.0

(51) Int. Cl.
*A61F 9/008* (2006.01)

(52) U.S. Cl.
CPC ..... *A61F 9/00804* (2013.01); *A61F 2009/00887* (2013.01)

(58) Field of Classification Search
CPC .......... A61F 9/00804; A61F 9/008; A61F 2009/00887; A61F 2009/00897; G02B 26/101; G02B 26/103
See application file for complete search history.

(56) References Cited

U.S. PATENT DOCUMENTS

| 5,782,609 A | 7/1998 | Ikemoto et al. |
| 6,191,520 B1 * | 2/2001 | Maruyama ............. H02N 2/106 310/366 |

(Continued)

FOREIGN PATENT DOCUMENTS

| CN | 2522830 Y | 11/2002 |
| EP | 2363742 A1 | 9/2011 |

(Continued)

OTHER PUBLICATIONS

Office Action (Notice of Grounds of Rejection) dated May 10, 2022, by the Japanese Patent Office in corresponding Japanese Patent Application No. 2021-521998, and an English Translation of the Office Action. (11 pages).

(Continued)

*Primary Examiner* — Nathan J Jenness
(74) *Attorney, Agent, or Firm* — BUCHANAN INGERSOLL & ROONEY PC

(57) ABSTRACT

The present disclosure relates to a positioning device for positioning an object in a positioning plane. To minimize the position error (contouring error) in a continuous orbital travel in contrast to two linear adjusters (X and Y) arranged at a right angle to each other, the positioning device includes two rotation drives having different diameters and an object receiver for receiving the object. The object receiver is coupled to a first of the two rotation drives, which in turn is coupled to the second of the two rotating drives so that the object receiver is rotatable about the axes of rotation (A2, A3) of both rotation drives that are offset in parallel, and is thereby adjustable in the positioning plane. A light processor having such a positioning device, and a method for laser eye surgery using such a light processor are also disclosed.

20 Claims, 3 Drawing Sheets

(56) References Cited

U.S. PATENT DOCUMENTS

| | | | |
|---|---|---|---|
| 6,296,649 B1 | 10/2001 | Hellenkamp | |
| 6,322,216 B1 * | 11/2001 | Yee | A61B 3/113 |
| | | | 606/5 |
| 6,575,962 B2 | 6/2003 | Hohla | |
| 2007/0232196 A1 * | 10/2007 | Camp | B23Q 1/5481 |
| | | | 451/11 |
| 2008/0247059 A1 * | 10/2008 | Dong | G02B 7/102 |
| | | | 359/696 |
| 2008/0249513 A1 * | 10/2008 | Vogler | A61F 9/00836 |
| | | | 606/5 |

FOREIGN PATENT DOCUMENTS

| | | |
|---|---|---|
| JP | 2004024900 A | 1/2004 |
| JP | 2004243078 A | 9/2004 |
| JP | 2007175545 A | 7/2007 |
| JP | 2013009819 A | 1/2013 |
| WO | 2012035031 A1 | 3/2012 |

OTHER PUBLICATIONS

International Search Report (PCT/ISA/210) and Written Opinion (PCT/ISA/237) dated Jan. 8, 2020, by the European Patent Office as the International Searching Authority for International Application No. PCT/EP2019/076046.

Office Action (Communication) dated Jun. 1, 2023, by the European Patent Office in corresponding European Patent Application No. 19 779 455.5, and an English Translation of the Office Action. (7 pages).

* cited by examiner

POSITIONING DEVICE, LIGHT PROCESSOR HAVING SUCH A POSITIONING DEVICE, AND METHOD FOR LASER EYE SURGERY USING SUCH A LIGHT PROCESSOR

The present invention relates to a positioning device for positioning an object in a positioning plane, a light processor having such a positioning device, and a method for laser eye surgery using such a light processor.

The term "laser eye surgery" describes a special eye surgery or laser eye surgical treatment in which refraction-based visual impairment can be corrected by ablating the cornea. With such visual impairment, the light is deflected by the curvature of the cornea and the eye lens and projected into the interior of the eye, where the focus is not exactly on the fovea, the place of sharpest vision on the retina in the eye, but in front of or behind it.

In "laser eye surgery", a very thin layer of the cornea is cut off and folded up, which then serves as a protection and promotes healing. A laser thereafter ablates the surface of the cornea, so that the optical properties of the eye change and the refractive power of the cornea is again optimally adjusted.

A cataract is a typically age-related clouding of the natural lens of the eye, where the light rays inside the eye can no longer be focused on the retina, so that sensitivity to light and glare increases, the vision becomes blurred or out of focus, sometimes images are seen double or colors appear gray. In cataract laser eye surgery, the clouded natural lens is removed and replaced with a clear intraocular lens. To reach the clouded lens, a femtosecond laser is used to make a small incision in the eye, where only the front lens cover is opened in a circular manner and the lens nucleus located in the so-called rear chamber of the eye is sucked off after comminution. The lens cover then remaining then serves as a "natural holder" for the new intraocular lens.

As part of this laser eye surgery, the laser beam is to be guided over the patient's cornea with high precision on a predetermined track or trajectory. Errors in positioning and exposure time of the laser beam on the patient's cornea can not only adversely affect the treatment outcome, but can also cause serious damage to the patient's eye.

If any trajectories or paths of motion in a plane are to be travelled, then two linear adjusters (X and Y) are typically used, which are arranged at a right angle to one another and the Y-adjuster is connected to the movable part of the X-adjuster. With a sinusoidal speed profile of the first axis (X) and a 90° phase-shifted sinusoidal speed profile of the second axis (Y), a circular trajectory can be realized. With a continuous orbital travel, both axes (X and Y) have to change direction twice, i.e. the full circle has a total of four turning points. Due to physical conditions (inertia, backlash, finite sensor resolution, finite controller speed, etc.) there is a certain dead time at the turning points, i.e. the change in direction does not take place infinitely quickly, but a phase of a standstill of the respective axis arises instead. This dead time results in a dynamic position error (contouring error), i.e. the full circle has a total of four defects.

Publication FISHER Charles, [et al]: "Cobra: A two-degree of freedom fiber optic positioning mechanism", "IEEE Aerospace conference, IEEE, 2009", pp. 1-11 discloses a further positioning device.

The invention is based on the object of providing a positioning device for positioning an object in a positioning plane which minimizes the position error (contouring error) in a continuous orbital travel in contrast to two linear adjusters (X and Y) arranged at a right angle to each other.

Furthermore, the invention is based on the object of providing a light processor and a method for laser eye surgery using such a light processor in order to avoid the dynamic position errors (contouring errors), known from perpendicularly arranged linear adjusters (X and Y) when the laser beam travels along an orbit in particular on the cornea of a patient.

To satisfy this object, the present invention provides the positioning device for positioning an object in a positioning plane according to claim 1, comprising: two rotation drives with different diameters and an object receiver for receiving the object, where the object receiver is coupled to a first of the two rotation drives, which in turn is coupled to the second of the two rotation drives, so that the object receiver can be rotated about the axes of rotation of both rotation drives that are arranged parallel and offset from one another and is thus adjustable in the positioning plane. The invention makes it possible to travel any trajectory (path of motion) in general, as well as to precisely travel a circular trajectory in particular. With the invention, no defect-related turning points are necessary. Circular trajectories can be traveled continuously and precisely. Due to the lack of turning points and therefore of dead times, the dynamic position error during the orbital travel can be reduced. In contrast to a uniaxial rotatory system, however, not only orbits, but also randomly desired trajectories can be travelled.

Advantageous further developments of the invention are the object of the dependent claims.

It can be useful to have the first rotation drive have a smaller diameter than the second rotation drive. In this way, the position of the object receiver can be controlled particularly easily.

It can be advantageous to have a path of motion of the object receiver extending around the axis of rotation of the first rotation drive enclose or intersect the axis of rotation of the second rotation drive. In this embodiment, the object receiver can be moved by respective actuation of the rotation drives to any point of the positioning plane within a circle which corresponds to the path of motion of the object receiver around the axis of rotation of the second rotation drive.

It can be useful to have the diameter of a (first) path of motion of the object receiver extending around the axis of rotation of the first rotation drive be at least half as large as the maximum diameter of a (second) path of motion of the object receiver extending around the axis of rotation of the second rotation drive. By adjusting the distance of the object receiver from the axis of rotation of the second rotation drive—by way of actuating the first rotation drive—the diameter of the second path of motion of the object receiver can be adjusted in a selective manner—from zero to twice the diameter of the first path of motion of the object receiver.

It can be useful to have the directions of rotation and/or speeds of rotation of the rotation drives be controllable independently of one another. As a result, the object receiver can in principle follow any trajectory within the positioning plane and within the second path of motion of the object receiver around the axis of rotation of the second rotation drive. The first rotation drive and/or the second rotation drive is/are preferably configured as a piezoelectric rotation drive.

It can be useful to have the first rotation drive and/or the second rotation drive be formed to be ring-shaped. In this embodiment, the object receiver can be arranged within the ring opening or aperture of the first rotation drive and the positioning device can be structured in an extremely compact manner.

However, it can also be helpful to have each ring-shaped rotation drive comprise two rings which can be rotated relative to one another, one of which is configured as a stator ring and the other as a rotor ring. This embodiment proves to be particularly compact and can be manufactured inexpensively.

It can also prove useful to have the stator ring of the first rotation drive be coupled in a rotationally fixed manner to the rotor ring of the second rotation drive, preferably by way of a releasable coupling.

It can be useful to have the object receiver be arranged on an inner circumference of the (rotor ring of the) first rotation drive. This embodiment as well proves to be particularly compact.

A further aspect of the present invention relates to a light processor according to claim 10, comprising a positioning device according to one of the preceding claims as well as a light-directing element which is arranged on or in the object receiver of the positioning device and can be adjusted in the positioning plane by way of the positioning device in order to direct a light beam, in particular a laser beam, onto an object to be processed by the light beam. A laser beam can be directed with the light processor particularly precisely along orbits onto an object to be processed or over its surface, respectively. For example, laser eye surgery requires very powerful lasers that are heavy and take up a large volume. Regardless of such restrictions, the light processor according to the invention enables particularly gentle and safe laser eye surgery of cataracts or refraction-based visual impairments by changing the corneal curvature of a patient, because only the light-directing element needs to be moved for deflecting the laser beam. The light-directing element can be configured, for example, as a mirror, prism, light guide, lens, objective or the like.

It can also be advantageous to have the light-directing element be arranged and/or alignable on or in the object receiver of the positioning device in such a way that the light beam runs parallel to the axes of rotation of both rotation drives. In this embodiment, particularly precise alignment of the light beam is possible, which is advantageous for the outcome of the procedure.

It can prove useful to have the light beam run through the ring opening of the first rotation drive and/or through the ring opening of the second rotation drive. This embodiment allows, for example, beam paths to be passed through the system.

It can also be useful to have the light-directing element be the laser light-emitting part of a laser, preferably a femtosecond laser. Such a laser is particularly suitable for treating cataracts or refraction-based visual impairments.

Another aspect of the present invention relates to the use of the light processor according to one of the claims 10 to 13 for treating cataracts or a refraction-based visual impairment by acting on the cornea of a patient by way of the light beam or laser beam, respectively.

Yet another aspect of the present invention relates to a method for laser eye surgery using the light processor according to one of claims 10 to 13, comprising the steps of:
 arranging the light processor at a distance from the cornea of a patient, preferably such that the positioning plane of the positioning device is aligned exactly or substantially perpendicular to a normal to the cornea of the patient;
 adjusting the light-directing element arranged in the object receiver of the positioning device in the positioning plane by way of the first rotation drive and/or the second rotation drive so that the light beam directed by the light-directing element travels a track that is circular at least in sections and/or arcuate at least in section and/or a track that is straight at least in sections on the patient's cornea for changing the corneal curvature of the patient.

It can prove useful to combine the positioning device with one or more linear drives or linear adjusters in order to facilitate travelling the linear trajectories.

Further preferred embodiments arise from combinations of the features disclosed in the claims, the drawings, and in the description.

Terms and Definitions

Path of Motion

The path of motion of the object receiver about the axis of rotation of the rotation drive corresponds to the imaginary circle that the object receiver describes with one complete revolution about the axis of rotation of the rotation drive.

Object Receiver

The term object receiver denotes a receptacle or holder for an object to be moved by the positioning device.

Positioning Plane

The plane in which the object receiver can be moved by actuating the rotation drives is referred to as the positioning plane. The positioning plane extends perpendicular to the axes of rotation of both rotation drives.

Light-directing element. A light-directing element is an element that is able to direct a light beam. The light-directing element is preferably configured as a mirror, prism, lens, light guide, objective or the like.

DETAILED DESCRIPTION OF THE PREFERRED EMBODIMENT

Figure 1:
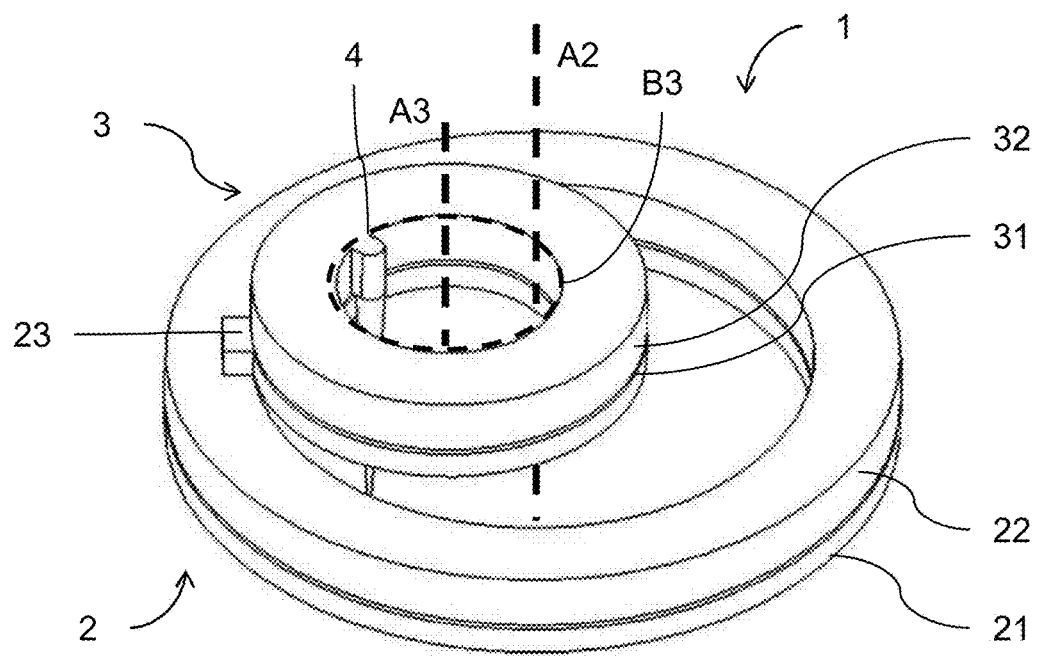
FIG. 1 shows a schematic and perspective view of a light processor according to the invention with a positioning device according to the invention comprising two ring-shaped rotation drives with different diameters.

The preferred embodiment of the invention, which shall be described in detail below with reference to the accompanying figures, relates to a light processor in the form of a laser eye surgical instrument, comprising a light-directing element in the form of a mirror or a light guide and a positioning device 1 according to the invention with two rotation drives 2, 3 of different diameters and an object receiver 4 in which the light-directing element is arranged.

This light-directing element is configured to direct a laser beam 5 for laser eye surgery onto cornea 6 of a patient, where the light-directing element is adjustable in the positioning plane by way of positioning device 1. In the present case, the light-directing element is the light-emitting part of a femtosecond laser for performing laser-assisted eye surgery.

Positioning device 1 according to the invention is used to position the light-directing element in a positioning plane. Object receiver 4, which receives the light-directing element, is coupled to first rotation drive 3 having a smaller diameter, which in turn is releasably coupled to second rotation drive 2 having a larger diameter, preferably by way of a coupling 23, so that object receiver 4 is arranged to be rotatable about rotational axes A2, A3, which are arranged parallel and offset to one another, and is therefore adjustable in the positioning plane.

Figure 6:
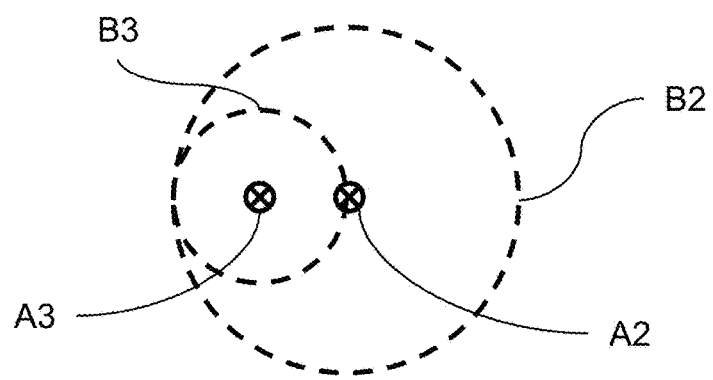
FIG. 6 shows a schematic top view along the axes of rotation of both rotation drives perpendicular onto the paths of motion of the object receiver around each of the two axes of rotation according to a preferred embodiment of the positioning device according to the invention.

As shown in FIG. 6, a path of motion B3 of object receiver 4 extending around axis of rotation A3 of first rotation drive 3 intersects axis of rotation A2 of second rotation drive 2. According thereto, the diameter of path of motion B3 of object receiver 4 extending around axis of rotation A3 of first rotation drive 3 is exactly half as large as the maximum diameter of a path of motion B2 of object receiver 4 extending around axis of rotation A2 of second rotation drive 2. This means that object receiver 4 or the light-directing element arranged thereon, respectively, can reach any position in the positioning plane that is within path of motion B2 of object receiver 4 extending around axis of rotation A2 of rotation drive 2 having a larger diameter.

For the reason the directions of rotation and the speeds of rotation of rotation drives 2, 3 can be controlled separately from one another, object receiver 4 can travel any trajectory within the positioning plane, in particular also circular, arcuate, or straight sections thereof.

In the present embodiment, each of two rotation drives 2, 3 is formed to be ring-shaped and comprises two rings 21, 31; 22, 32, of which one is configured as a stator ring 21, 31 and the other as a rotor ring 22, 32. Stator ring 31 of first rotation drive 3 is preferably coupled in a rotationally fixed manner to rotor ring 22 of second rotation drive 2 by way of releasable coupling 23, and object receiver 4 is arranged on an inner circumference of rotor ring 32 of first rotation drive 3.

The light-directing element is arranged in object receiver 4 of positioning device 1 in such a way that laser beam 5 runs parallel to axes of rotation A2, A3 of the two rotation drives 2, 3. Laser beam 5 is guided through the ring opening of both rotation drives in order to impinge on a target object 6 arranged thereunder in the operating state (cf. FIGS. 2, 4, 5).

Figure 2:
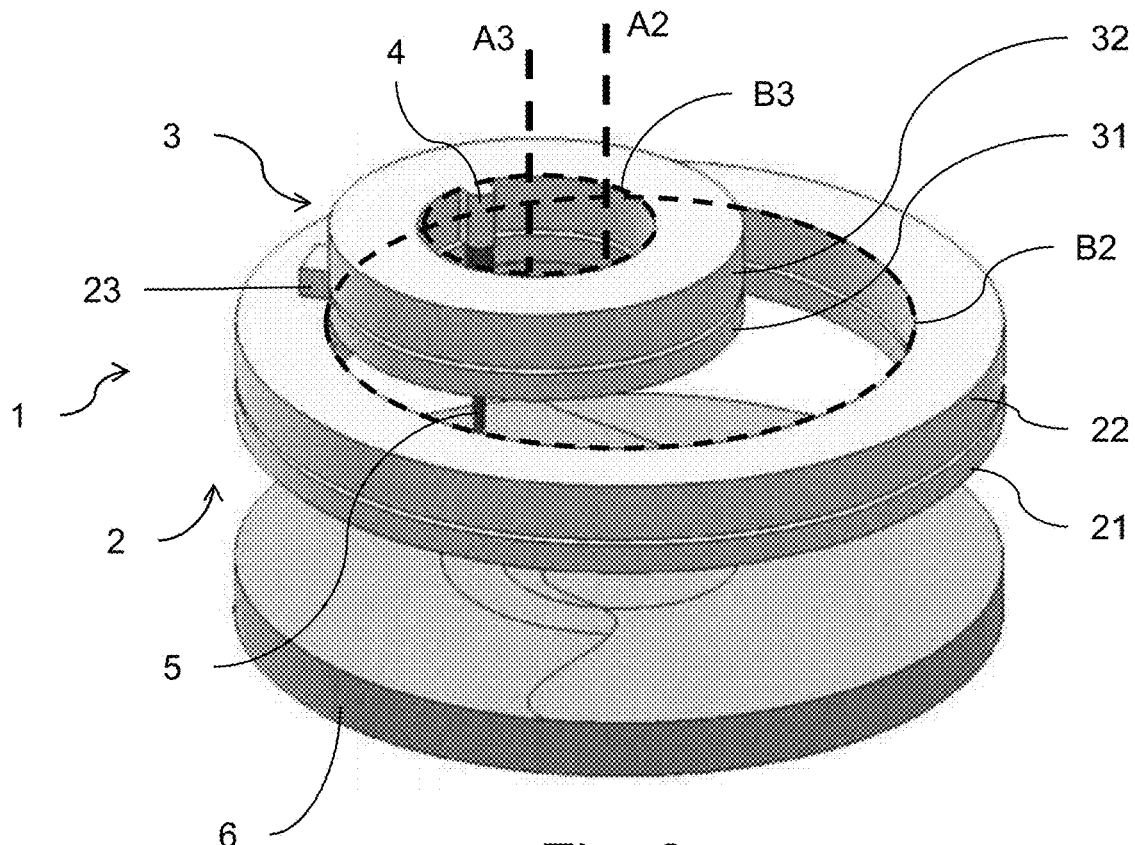
FIG. 2 shows a schematic and perspective view of the light processor according to FIG. 1 for laser eye surgery, where a light-directing element is adjusted in a positioning plane by the positioning device by actuating the two rotation drives in order to guide the light beam directed by the light-directing element along a trajectory that is at least in sections circular over the cornea of a patient.
Figure 3:
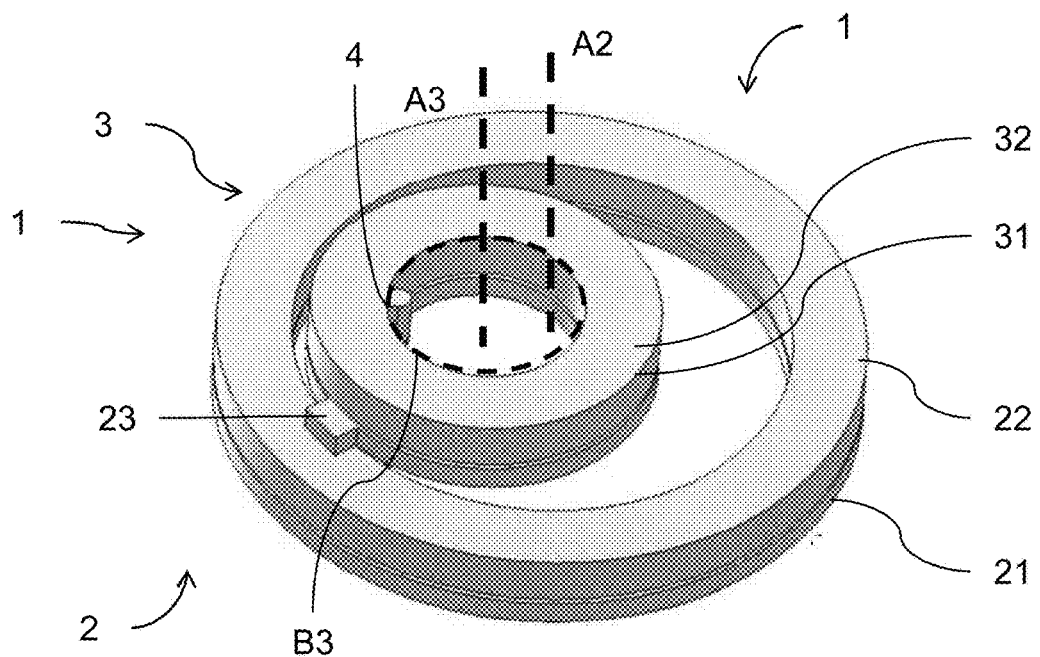
FIG. 3 shows a schematic and perspective view similar to FIG. 1.
Figure 4:
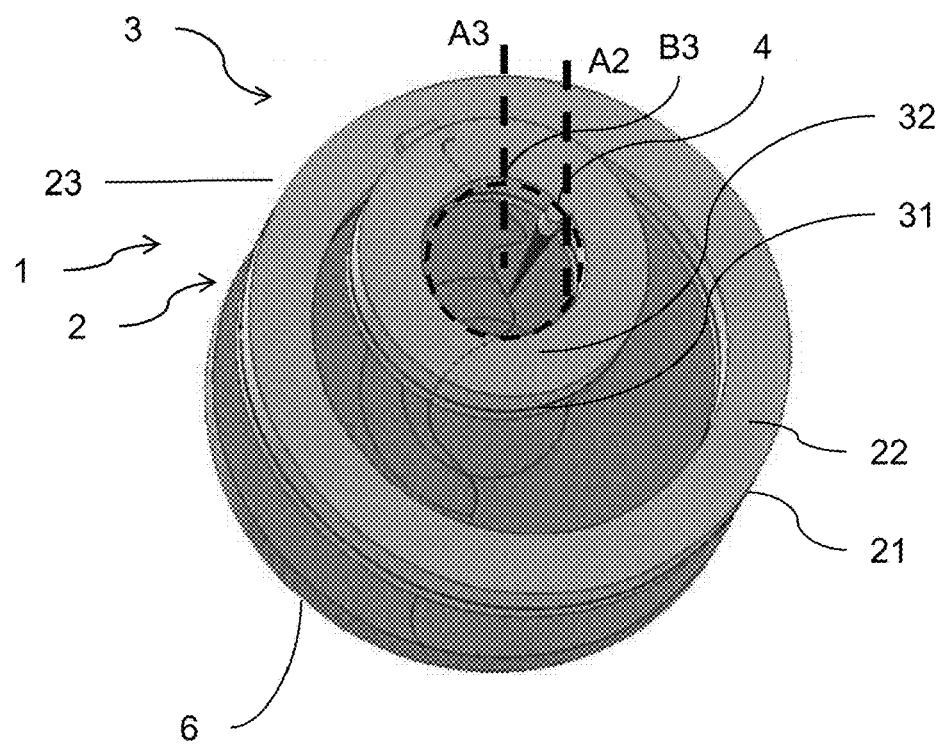
FIG. 4 shows a schematic and perspective view similar to FIG. 2 from a different viewing angle.
Figure 5:
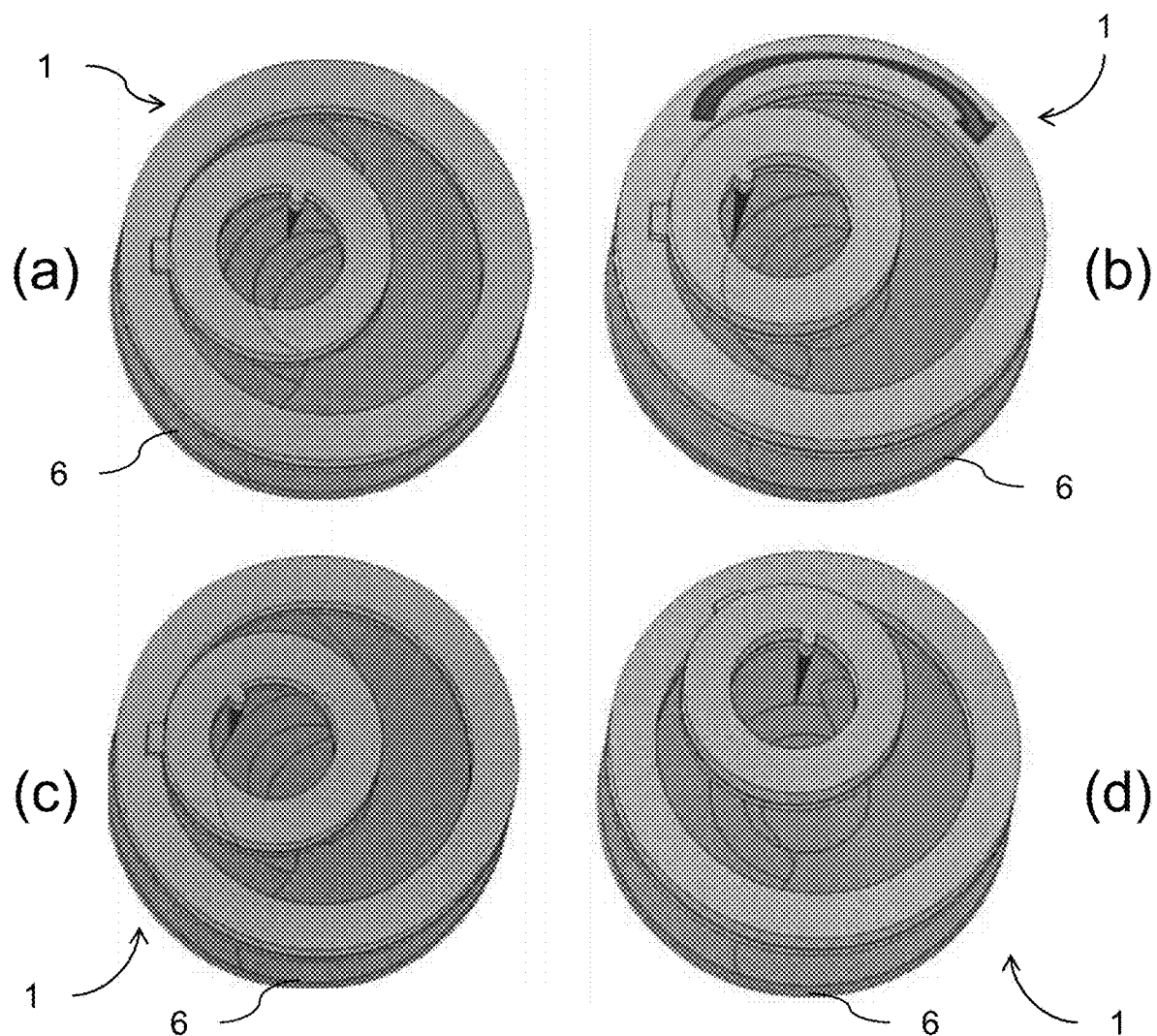
FIG. 5 shows, in views (a) to (d), different stages of laser eye surgery using the light processor according to one of the FIGS. 1 to 4.

According to the method of the invention for laser eye surgery, the light processor according to the invention is arranged at a distance from cornea 6 of a patient so that the positioning plane of positioning device 1 is ideally aligned exactly or substantially perpendicular to a normal to cornea 6 of the patient (cf. FIGS. 2, 4, 5). The light-directing element arranged in object receiver 4 of positioning device 1 is thereafter adjusted in the positioning plane by actuating both rotation drives, so that laser beam 5 directed by the light-directing element travels a track on cornea 6 of the patient which can contain circular, arcuate, or straight path sections for changing the patient's corneal curvature or make incisions in the patient's cornea. Individual stages of this procedure are shown in views (a) to (d) in FIG. 5.

By rotating or adjusting first rotation drive 3, different circle diameters can be set in a selective manner. By rotating or adjusting second rotation drive 2, orbits with the previously set circle diameter can be traveled continuously. The combined rotation of first and second rotation drive 2, 3 allows for any desired trajectory to be travelled.

LIST OF REFERENCE CHARACTERS 1 positioning device
2 second rotation drive (large diameter)
3 first rotation drive (small diameter)
4 object receiver
5 beam path or light beam or laser beam, respectively
6 target object or cornea, respectively
21 stator ring of the second rotation drive (large diameter)
22 rotor ring of the second rotation drive (large diameter)
23 coupling section
31 stator ring of the first rotation drive (small diameter)
32 rotor ring of the first rotation drive (small diameter)
A2 axis of rotation of the second rotation drive (large diameter)
A3 axis of rotation of the first rotation drive (small diameter)
B2 path of motion of the object receiver about the axis of rotation A2
B3 path of motion of the object receiver about the axis of rotation A3

The invention claimed is:

1. A positioning device for positioning an object in a positioning plane, the positioning device comprising:
   two rotation drives having different diameters; and
   an object receiver for receiving an object, where said object receiver is coupled to a first of said two rotation drives and said first of said two rotation drives is coupled to a second of said two rotation drives, so that said object receiver is configured to be rotated about axes of rotation of both rotation drives that are arranged parallel and offset from one another, and is adjustable in said positioning plane,
   wherein said first rotation drive and/or said second rotation drive is/are ring-shaped, wherein each ring-shaped rotation drive includes:
      two rings rotatable relative to one another, one of which is formed as a stator ring and another of which is formed as a rotor ring, and
   wherein said first rotation drive and/or said second rotation drive is/are configured as a piezoelectric rotation drive.

2. The positioning device according to claim 1, wherein said first rotation drive has a smaller diameter than said second rotation drive.

3. The positioning device according to claim 2, wherein a path of motion of said object receiver extending around said axis of rotation of said first rotation drive encloses or intersects said axis of rotation of said second rotation drive.

4. The positioning device according to claim 3, wherein a diameter of a path of motion of said object receiver extending around said axis of rotation of said first rotation drive is at least half as large as a maximum diameter of a path of motion of said object receiver extending around said axis of rotation of said second rotation drive.

5. The positioning device according to claim 4, wherein said first and second rotation drives are configured such that directions of rotation and/or speeds of rotation of said first and second rotation drives are controllable separately from one another.

6. The positioning device according to claim 1, wherein a path of motion of said object receiver extending around said axis of rotation of said first rotation drive encloses or intersects said axis of rotation of said second rotation drive.

7. The positioning device according to claim 1, wherein a diameter of a path of motion of said object receiver extending around said axis of rotation of said first rotation drive is at least half as large as a maximum diameter of a path of motion of said object receiver extending around said axis of rotation of said second rotation drive.

8. The positioning device according to claim 1, wherein said first and second rotation drives are configured such that directions of rotation and/or speeds of rotation of said first and second rotation drives are controllable separately from one another.

9. The positioning device according to claim 1, wherein said stator ring of said first rotation drive is coupled in a rotationally fixed manner to said rotor ring of said second rotation drive, by a releasable coupling.

10. The positioning device according to claim 1, wherein said object receiver is arranged on an inner circumference of said first rotation drive.

11. A light processor comprising, in combination:
a positioning device according to claim 1; and
a light-directing element which is arranged on said object receiver of said positioning device and configured to be adjustable in said positioning plane by way of said positioning device in order to direct a light beam onto an object to be processed by said light beam.

12. The light processor combination according to claim 11, wherein said light-directing element is arranged and/or alignable on said object receiver of said positioning device such that said light beam will extend parallel to said axes of rotation of both rotation drives.

13. The light processor combination according to claim 11, wherein the positioning device for positioning an object in a positioning plane includes the two rotation drives having different diameters and the object receiver for receiving said object, where said object receiver is coupled to the first of said two rotation drives and said first of said two rotation drives is coupled to the second of said two rotation drives, so that said object receiver is rotatable about the axes of rotation of both rotation drives that are arranged parallel and offset from one another, and is configured to be adjustable in said positioning plane, wherein said first rotation drive and/or said second rotation drive is/are ring-shaped and is arranged such that said light beam will be guided through a ring opening of said first rotation drive and/or through a ring opening of said second rotation drive.

14. The light processor combination according to claim 11, wherein said light-directing element is the laser light-emitting part of a laser.

15. The light processor combination according to claim 11, wherein said light-directing element is the laser light-emitting part of a femtosecond laser.

16. The positioning device of claim 1, wherein each ring-shaped rotation drive includes a first ring and a second ring, the first ring rotatable relative to the second ring, wherein the first ring is formed as the rotor ring and the second ring is formed as the stator ring, and wherein the first ring includes a first ring opening and the second ring includes a second ring opening, the first ring opening and second ring opening forming a continuous opening through the first ring and the second ring.

17. A method for treating cataract or a refraction-based visual impairment, the method comprising:
adjusting a positioning device having two rotation drives having different diameters, and an object receiver for receiving an object, where said object receiver is coupled to a first of said two rotation drives and said first of said two rotation drives is coupled to a second of said two rotation drives, so that said object receiver is configured to be rotated about axes of rotation of both rotation drives, that are arranged parallel and offset from one another, and is adjustable in said positioning plane, wherein said first rotation drive and/or said second rotation drive is/are ring-shaped, wherein each ring-shaped rotation drive includes two rings rotatable relative to one another, one of which is formed as a stator ring and another of which is formed as a rotor ring, and wherein said first rotation drive and/or said second rotation drive is/are configured as a piezoelectric rotation drive;
arranging a light-directing element on said object receiver of said positioning device and adjusting the light-directing element in said positioning plane by way of said positioning device in order to direct a light beam onto an object to be processed by said light beam; and
acting on the cornea of a patient by way of said light beam in the form of a laser beam.

18. The method of claim 17, wherein each ring-shaped rotation drive includes a first ring and a second ring, the first ring rotatable relative to the second ring, wherein the first ring is formed as the rotor ring and the second ring is formed as the stator ring, and wherein the first ring includes a first ring opening and the second ring includes a second ring opening, the first ring opening and second ring opening forming a continuous opening through the first ring and the second ring.

19. A method for laser eye surgery using a light processor including a positioning device for positioning an object in a positioning plane, the positioning device including two rotation drives having different diameters and an object receiver for receiving an object, where said object receiver is coupled to a first of said two rotation drives, and said first of said two rotation drives is coupled to a second of said two rotation drives, so that said object receiver is configured to be rotated about axes of rotation of both rotation drives that are arranged parallel and offset from one another, and is adjustable in said positioning plane, wherein said first rotation drive and/or said second rotation drive is/are ring-shaped, wherein each ring-shaped rotation drive includes two rings rotatable relative to one another, one of which is formed as a stator ring and another of which is formed as a rotor ring, and wherein said first rotation drive and/or said second rotation drive is/are configured as a piezoelectric rotation drive, the light processor including a light-directing element which is arranged on said object receiver of said positioning device and configured to be adjustable in said positioning plane by way of said positioning device in order to direct a light beam onto an object to be processed by said light beam, the method comprising:
a. arranging said light processor at a distance from a cornea of a patient, such that a positioning plane of the positioning device is aligned exactly or substantially perpendicular to a normal to said cornea of the patient; and
b. adjusting the light-directing element arranged in the object receiver of said positioning device in the positioning plane by way of the first rotation drive and/or a second rotation drive so that the light beam directed by said light-directing element travels a track that is circular at least in sections and/or arcuate at least in section and/or or a track that is straight at least in sections on said cornea of the patient for changing a corneal curvature of the patient.

20. The method of claim 19, wherein each ring-shaped rotation drive includes a first ring and a second ring, the first ring rotatable relative to the second ring, wherein the first ring is formed as the rotor ring and the second ring is formed as the stator ring, and wherein the first ring includes a first ring opening and the second ring includes a second ring opening, the first ring opening and second ring opening forming a continuous opening through the first ring and the second ring.

* * * * *